(12) United States Patent
Patten et al.

(10) Patent No.: US 9,557,255 B2
(45) Date of Patent: Jan. 31, 2017

(54) TENSION MEMBER FATIGUE TESTER USING TRANSVERSE RESONANCE

(71) Applicant: X Development LLC, Mountain View, CA (US)

(72) Inventors: Elias Wolfgang Patten, Seattle, WA (US); Damon Vander Lind, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 15/159,111

(22) Filed: May 19, 2016

(65) Prior Publication Data
US 2016/0258851 A1 Sep. 8, 2016

Related U.S. Application Data

(63) Continuation of application No. 14/066,667, filed on Oct. 29, 2013, now Pat. No. 9,372,137.
(Continued)

(51) Int. Cl.
*G01N 3/02* (2006.01)
*G01N 3/32* (2006.01)
(Continued)

(52) U.S. Cl.
CPC ........ *G01N 3/02* (2013.01); *G01N 3/32* (2013.01); *G01N 3/04* (2013.01); *G01N 3/08* (2013.01);
(Continued)

(58) Field of Classification Search
CPC .............. G01N 3/02; G01N 3/04; G01N 3/08; G01N 3/10; G01N 3/32; G01N 2203/0017; G01N 2203/0254; G01N 2203/0005; G01N 2203/0016
(Continued)

(56) References Cited

U.S. PATENT DOCUMENTS 1,948,104 A 2/1934 Firestone et al.
1,952,953 A 3/1934 Templin
(Continued)

FOREIGN PATENT DOCUMENTS

AT 501168 A4 7/2006
WO 2006116782 A1 11/2006

OTHER PUBLICATIONS

Hobbs, R.E. and Ghavami, K., The Fatigue of Structural Wire Strands, Int. J. Fatigue, Apr. 1982, pp. 69-72, Butterworth & Co. Ltd.
(Continued)

*Primary Examiner* — Lisa Caputo
*Assistant Examiner* — Jonathan Dunlap
(74) *Attorney, Agent, or Firm* — McDonnell Boehnen Hulbert & Berghoff LLP (57) ABSTRACT

A system includes: a tension member having a first end and a second end, where the first end of the tension member is connected to a first loading member and the second end of the tension member is connected to a second loading member; a first actuator configured to translate the first loading member, such that a tensile load is applied to the tension member along a first direction; a second actuator configured to translate the second loading member in two or more second directions that are substantially transverse to the first direction; and a control system that is configured to control the second actuator, such that the second loading member oscillates between the two or more second directions, where the oscillation of the second loading member causes the tension member to vibrate at a frequency.

20 Claims, 6 Drawing Sheets

Related U.S. Application Data (60) Provisional application No. 61/867,917, filed on Aug. 20, 2013.

(51) Int. Cl.
G01N 3/04 (2006.01)
G01N 3/10 (2006.01)
G01N 3/08 (2006.01)

(52) U.S. Cl.
CPC ......... *G01N 3/10* (2013.01); *G01N 2203/0005* (2013.01); *G01N 2203/0016* (2013.01); *G01N 2203/0017* (2013.01); *G01N 2203/0254* (2013.01)

(58) Field of Classification Search
USPC .................. 73/826, 828, 829, 831, 836, 837
See application file for complete search history.

(56) References Cited

U.S. PATENT DOCUMENTS

| | | | |
|---|---|---|---|
| 3,442,120 A | 5/1969 | Russenberger et al. |
| 3,664,179 A | 5/1972 | Danko et al. |
| 3,714,821 A | 2/1973 | Gilley |
| 4,056,974 A | 11/1977 | Klinger et al. |
| 4,878,417 A | 11/1989 | Facon |
| 4,899,602 A | 2/1990 | Fender |
| 5,305,645 A | 4/1994 | Reifsnider et al. |
| 6,622,571 B2 | 9/2003 | Chen |
| 6,718,833 B2 | 4/2004 | Xie |
| 7,953,561 B2 | 5/2011 | Musial et al. |
| 2005/0204826 A1 | 9/2005 | Scarborough |
| 2008/0006097 A1 | 1/2008 | Stauffer et al. |
| 2008/0223145 A1 | 9/2008 | Merendino |
| 2010/0275695 A1 | 11/2010 | Cotrell et al. |
| 2011/0041617 A1 | 2/2011 | Cotrell et al. |

OTHER PUBLICATIONS

White, D., Musial, W., and Engberg, S., Evaluation of the New B-REX Fatigue Testing System for Multi-Megawatt Wind Turbine Blades, National Renewable Energy Laboratory, Dec. 2004, 17 pages.

Brondsted, P., Lilholt, H., and Lystrup, A., Composite Materials for Wind Power Turbine Blades, Annual Review of Materials Research, pp. 505-538 and C1-C5, vol. 35, 2005.

McKewan, W. and Miscoe, A., Baseline Tensile Testing at the Wire Rope Research Laboratory, U.S. Dept. of the Interior, Bureau of Mines, Information Circular 9255, 5 pages.

Weibull, Chapter III, Fatigue Testing Machines and Equipments, Fatigue Testing and Analysis of Results, 1960, pp. 25-65.

Gustafson, C. and Echtermeyer, A., Long-Term Properties of Carbon Fibre Composite Tethers, International Journal of Fatigue, 28, 2006, pp. 1353-1362, Elsevier Ltd.

Koeberl, B., A Novel Fatigue Testing Facility, 6th International Ph.D. Symposium in Civil Engineering, Aug. 2006, pp. 80-81.

Composite Rigging, Paprec-Virbac Post Barcelona Race Inspection, Apr. 23, 2008, Southern Spars, pp. 1-6.

International Preliminary Report on Patentability (Translation), Kollegger and Koeberl International Application No. PCT/AT2006/000173, International Filing Date Apr. 27, 2006.

White, D., New Method for Dual-Axis Fatigue Testing of Large Wind Turbine Blades Using Resonance Excitation and Spectral Loading, National Renewable Energy Laboratory, Apr. 2004, 195 pages.

Pendered, J. and Bishop, R., A Critical Introduction to Some Industrial Resonance Testing Techniques, Journal Mechanical Engineering Science, vol. 5, No. 4, 1963, pp. 345-367.

Koeberl, B. and Kollegger, J., High Frequency Testing Facility for Stay Cables and Tendons, Structural Engineering International, Mar. 2008, pp. 259-264.

Symposium on Large Fatigue Testing Machines and Their Results, Sixtieth Annual Meeting Papers, ASTM Special Technical Publication, American Society for Testing Materials, Philadelphia, PA, Jun. 1957.

TENSION MEMBER FATIGUE TESTER USING TRANSVERSE RESONANCE

CROSS-REFERENCE TO RELATED APPLICATION

The present application claims the benefit of U.S. Provisional Application No. 61/867,917, filed Aug. 20, 2013 and U.S. patent application Ser. No. 14/066,667, filed Oct. 29, 2013. The entire content of the aforementioned applications are herewith incorporated by reference into the present application.

BACKGROUND

Unless otherwise indicated herein, the materials described in this section are not prior art to the claims in this application and are not admitted to be prior art by inclusion in this section.

Tension members, such as tethers, umbilicals, ropes, and cables, are used to support loads associated with overhead transmission lines, suspension bridges, aerostats, offshore drilling platforms, and towing and mining applications, among other uses. In many such applications, the tension members undergo repeated loading, often at very high load values and over a large number of cycles. Thus, a testing system is useful to repeatedly test tension members under anticipated load conditions. Information from such tests may help to determine, for example, how well a tension member product or design will hold up in fatigue.

SUMMARY

Various tension member test systems and methods for the fatigue testing of tension members are disclosed herein. Specifically, a tension member under tension could be tested by displacing one end of the tension member back and forth in at least one direction substantially transverse to the long axis of the tension member. Such displacements may induce the tension member to vibrate at a frequency. The frequency could relate to a resonant frequency of the loading system.

In a first aspect, a system is provided. The system includes a tension member having a first end and a second end. The first end of the tension member is connected to a first loading member and the second end of the tension member is connected to a second loading member. The system also includes a load cell, a first actuator, a second actuator and a control system having a processor and a memory. The processor is configured to execute instructions stored in the memory so as to carry out operations. The operations include controlling the first actuator to displace the first loading member based on information received from the load cell such that a tensile load is applied to the tension member along a first direction. The operations also include controlling the second actuator to displace the second loading member based on a desired cyclic loading profile such that the second loading member oscillates between two or more second directions. The oscillation of the second loading member causes the tension member to vibrate at a frequency. The desired cyclic loading profile includes a base load and a peak load.

In a second aspect, a method is provided. The method includes controlling a first actuator to displace a first loading member based on information received from a load cell such that a tensile load is applied to a tension member along a first direction. The tension member has a first end and a second end. The first end of the tension member is connected to the first loading member and the second end of the tension member is connected to a second loading member. The method also includes controlling a second actuator to displace the second loading member based on a desired cyclic loading profile such that the second loading member oscillates between two or more second directions. The oscillation of the second loading member causes the tension member to vibrate at a frequency. The desired cyclic loading profile includes a base load and a peak load.

In further aspects, any type of device could be used or configured as a means for performing functions of any of the methods described herein (or any portions of the methods described herein). For example, various mechanical apparatuses could be used to apply a base tension load to a tension member using any type of a first loading member along a first direction. Furthermore, any type of a second loading member could displace the tension member in a direction substantially transverse to the first direction so as to vibrate the tension member at a frequency.

These as well as other aspects, advantages, and alternatives, will become apparent to those of ordinary skill in the art by reading the following detailed description, with reference where appropriate to the accompanying drawings.

DETAILED DESCRIPTION

Illustrative methods and systems are described herein. The illustrative embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

I. Overview

In an Airborne Wind Turbine (AWT) system, an aerial vehicle may convert kinetic wind energy to electrical energy. The aerial vehicle may be connected to a ground station via a tether so that (i) the aerial vehicle can take off from the ground station, fly at a range of elevations (for example, in a substantially circular path), land at the ground station, and (ii) conduct electrical current to the ground station. In some situations, the ground station may transmit electricity to the aerial vehicle (for example, during take-off, landing, and/or low wind conditions). The tether could also be configured to transmit other kinds of signals.

Illustrative embodiments may generally relate to or take the form of systems and methods for testing tethers that can be used in AWTs. More generally, such testing systems and methods may be utilized to test "tension members." Tension members may include, but are not limited to, tethers (and associated connection hardware) utilized in a wind energy system such as an AWT, as well as other types of cables or lines.

Such testing systems and methods could cause a tension member to vibrate in a transverse fashion while under tension, similar to a plucked guitar string. In some embodiments, systems and methods could cause the tension member to vibrate at or near a resonant frequency. The resonant frequency could relate to a resonance arising due to a combination of loading system elements and/or the environment.

The tension member could vibrate in a transverse mode or transverse direction. A transverse mode could be, for example, a vibration of the tension member where the vibration has an amplitude perpendicular, or transverse, to the long axis of the tension member. By causing the tension member to vibrate in such a manner, the tension force on the tension member may vary in a periodic fashion. Tension members may include, but are not limited to, tethers (and associated connection hardware) utilized in a wind energy system such as an AWT.

In an illustrative AWT system, a tensile load on the tether (and, in some examples, its connections to the aerial vehicle) may vary. For example, the tensile load on the tether may vary based on aerodynamic and gravitational forces acting on the aerial vehicle and/or one or more turbines connected to the aerial vehicle. Specifically, the aerodynamic forces acting on the aerial vehicle may vary based on factors such as the net thrust or drag of the turbines, control surface configuration, altitude, relative wind speed/direction, and/or flight speed of the aerial vehicle.

Additionally, variations in tensile load on the tether could occur in a periodic manner, such as during circular flight. In particular, the load on the tether could vary periodically during normal "cross-wind" flight where the aerial vehicle flies in a substantially circular flight path. In some embodiments, a time period of a single circular flight cycle, and thus the periodic variation of tensile load on the tether, could be between 14 to 19 seconds. Further, in some embodiments, the tensile load on the tether may vary by about 50% during the circular flight cycle of the aerial vehicle.

In the foregoing example, the tether may experience more than two million cycles of tensile loading between 100,000 and 220,000 Newtons (N) per year due to circular flight cycles alone. Further, the tensile load on the tether may vary in other ways as well. For example, the tensile load on the tether may vary when the ground station retrieves the aerial vehicle by reeling in the tether. Such repeated variations in tensile loading may cause the tether to fail (e.g., rupture, tear, crack, rip, or otherwise not function as part of an AWT).

Embodiments described herein may be used to test one or more parameters of a tether, such as fatigue performance, stiffness, maximum static load capability, and/or strength, by loading the tether before or after it is used as part of an AWT system.

Beneficially, the embodiments described herein may be used to test fatigue performance of a tether in a time period that is shorter than a desired lifespan of an AWT tether. For instance, in some implementations, fatigue performance of a tether with a desired life of two years as part of an AWT may be tested in four days. As a result, the time that is needed to design and/or evaluate new tether designs may be reduced. Further, embodiments may help to achieve such time savings while at the same time reducing the cost of such testing by, e.g., reducing the size and/or complexity of testing components. Finally, due to such time savings, more tests may be performed in a given period of time, which could improve the confidence level of data gathered from such systems and methods. Accordingly, the system and methods disclosed here could provide better ways to help: 1) evaluate and compare performance of different tether and termination designs; 2) uncover flaws in manufacturing or design of such tethers earlier in the testing process; and 3) build confidence in tether/termination design and overall system design.

II. Illustrative Systems

Figure 1:
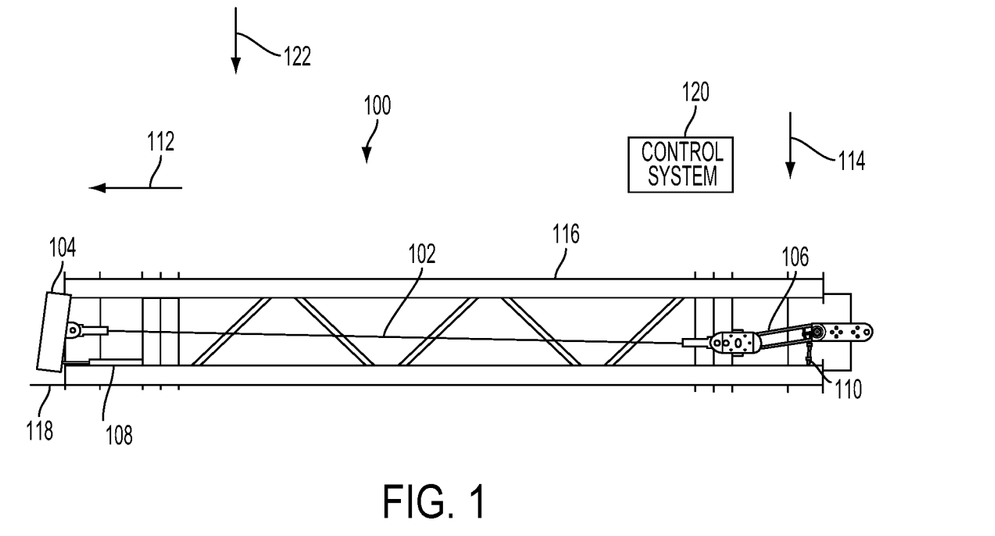
FIG. 1 is a diagram illustrating a transverse resonance fatigue test system, according to an illustrative embodiment.

FIG. 1 is a simplified diagram illustrating a testing system 100 according to an illustrative embodiment. As shown, the testing system 100 includes a first loading member 104, a first actuator 108, a second loading member 106, a second actuator 110, and a control system 120. Further, as shown in FIG. 1, a tension member 102 has a first end that is connected to the first loading member 104 and a second end that is connected to the second loading member 106.

In some implementations, the first actuator 108 may be configured to displace the first loading member 104, such that a tensile load (e.g., an initial base load) is applied to the tension member 102 along a first direction 112. In some examples, the first actuator 108 may displace the first loading member 104 by applying one or more forces to the first loading member 104.

Moreover, in some implementations, the second actuator 110 may be configured to displace the second loading member 106 back and forth in two or more second directions 114, such that the two or more second directions 114 are substantially transverse to the first direction 112. Such displacement could be likened to that of wiggling a free end of a taut string, the other end of which is fastened to a wall. In an example implementation, the second actuator 110 could have a stroke length of three inches, although other implementations are possible.

The term "substantially transverse," as used in this disclosure, refers to exactly transverse and/or one or more deviations from exactly transverse that do not significantly impact testing a tension member as described herein.

Further, in some implementations, the control system 120 may be configured to control the second actuator 110, such that the displacement of the second loading member 106 causes the tension member 102 to vibrate at a particular frequency, such as a resonant frequency of a combination of loading system elements that could include the tension member 102. The resonant frequency may vary based, at least in part, on a change in the stiffness of the loading system. Such a change in stiffness may be due to an amount of deflection of the tension member 102 and/or the second loading member 106. As a result, the control system 120 may control the second actuator 110 to (i) cause vibration of the loading system at its resonant frequency; and (ii) maintain the amplitude of vibration by controlling the amount of energy gained or lost by the loading system (for example by controlling the magnitude or duty cycle of the input force from the second actuator 110).

For example, the control system 120 could be configured control the second actuator 110 so as to cause the tension member 102 to vibrate in a transverse mode. In some examples, the control system 120 may be configured to control the second actuator 110 based on at least one angular position of the second loading member 106 during the displacement cycle.

Further still, in some implementations, repeated displacement cycles of the second loading member 106 may cause the tension member 102 to be periodically loaded substantially in tension. Beneficially, such loading (rather than, for example, directly pulling a middle portion of the tension member 102) may reduce local compressive stress in the tension member 102 that could affect testing of one or more parameters of the tension member 102. Moreover, such an illustrative configuration may beneficially permit testing of fatigue performance of tension members at high frequencies, which may increase the speed of evaluating and/or designing such tension members.

The term "substantially in," as used in this disclosure, refers to exactly in and/or one or more deviations from exactly in that do not significantly impact testing a tension member as described herein.

Additionally, as shown in FIG. 1, the system 100 may further include a frame 116. Further, as shown in FIG. 1, the first loading member 104 may be connected to the tension member 102 via a first connection location and the first loading member 104 may connected to the frame via a second connection location; and the second loading member 106 may be connected to the tension member 102 via a first connection location and the second load member 106 could be connected to the frame 116 via a second connection location. In some embodiments, the second loading member 106 could be rotatably connected to the frame 116 and/or the second end of the tension member 102 via cylindrical roller bearings (not shown).

In some implementations, the frame 116 may be configured to resist one or more tensile forces and/or compressive forces based on the displacement of the first loading member 104 and the displacement of the second loading member 106. The frame 116 could include, for example, a four-member compression frame with lacings and battens. In some embodiments, the frame 116 could be made of structural steel. However, the frame 116 could include different structural elements or materials.

As shown in FIG. 1, the frame 116 (and correspondingly, the first direction 112) could be oriented substantially parallel to the ground 118. In such embodiments, the displacement of the second loading member 106 may be substantially perpendicular to the ground 118 (e.g., the second loading member could be configured to move up and down relative to the ground 118). Alternatively, the displacement of the second loading member 106 may be substantially parallel to the ground 118 (e.g., side-to-side with respect to the first direction 112). In such implementations, when the displacement of the second loading member 106 is substantially parallel to the ground 118, the system might include cables and/or beams configured to reduce at least one out-of-plane and/or rotational mode of vibration of the tension member 102 during the displacement of the second loading member 106. In other words, the long axis of tension member 102 could be substantially parallel or perpendicular to a gravitational force vector 122. Accordingly, based at least in part to the orientation of the frame 116, the vibration of tension member 102 could be affected by gravitational force during vibration.

In other examples, the frame 116 may be oriented such that the first direction 112 is substantially perpendicular to the ground 118. In such examples, the displacement of the second loading member 106 may be substantially parallel to the ground. In other examples, the first loading member 104 and/or the second loading member 106 may be connected to the ground or any other type of fixture. In such examples, the system might not include a frame 116.

The term "substantially parallel," as used in this disclosure, refers to exactly parallel and/or one or more deviations from exactly parallel that do not significantly impact testing a tension member as described herein. Further, the term "substantially perpendicular," as used in this disclosure, refers to exactly perpendicular and/or one or more deviations from exactly perpendicular that do not significantly impact testing a tension member as described herein.

Although FIG. 1 shows one tension member 102 connected to the first loading member 104 and the second loading member 106, in other examples, two or more tension members 102 may be connected to the first loading member 104 and the second loading member 106.

Figure 2A:
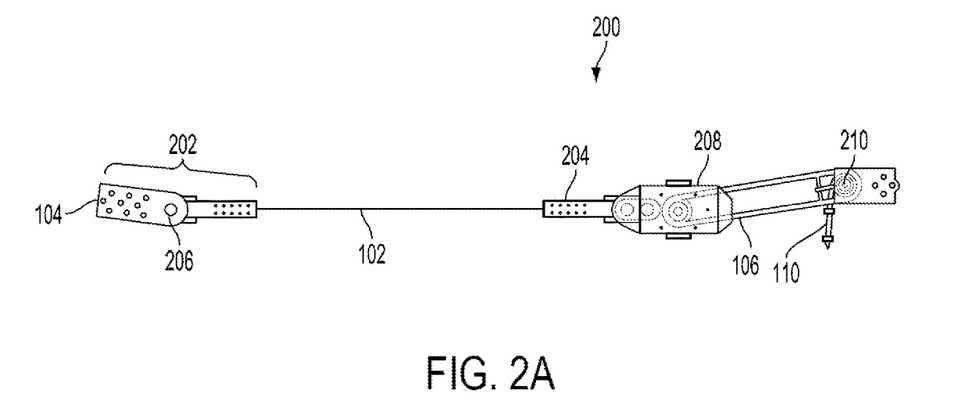
FIG. 2A is a diagram illustrating details of the transverse resonance fatigue test system, according to an illustrative embodiment.

FIG. 2A is a simplified diagram illustrating selected details of the testing system 200. The system may further include one or more termination assemblies 202 & 204, a coupler 208, a first sensor 206, and a second sensor 210. Specifically, the first and/or second ends of the tension member 102 could include termination assemblies 202 & 204. Termination assemblies 202 & 204 could include potted termination fixtures, although other types of termination assemblies are possible. As shown in FIGS. 1 and 2A, the first end of the tension member 102 is connected to the termination assembly 202. Thus, in some embodiments, the first end of the tension member is connected to the first loading member 206 via the termination assembly 202. In some implementations, the testing system could be configured to test at least the combination of the termination assemblies 202 & 204 and the tension member 102.

Further, as shown in FIG. 2A, the second end of the tension member is connected to the coupler 208 via termination assembly 204. In some embodiments, the second end of the tension member 102 is connected to the second loading member 106 via the coupler 208. In some examples, the coupler 208 may be further configured to receive one or more weights (not shown). In some examples, various elements of the system 200 could be likened to a harmonic oscillator. In such a situation, the tension member 102 and the weight applied to the coupler 208 could be treated like the spring and mass in such a harmonic oscillator. By displacing the tension member 102, the system could act similar to a driven harmonic oscillator system. As such, adding one or more weights to the coupler 208 could affect the testing of the tension member 102 (e.g., by modifying a resonant frequency of the loading system, which acts as a harmonic oscillator system).

Additionally, as shown in FIG. 2A, the first sensor 206 could include a load cell (not shown) that senses stress (or force) information. For example, the first end of the tension member 102 could be connected to the first loading member 104 via the first sensor 206. In such a scenario, the first sensor 206 could be configured to sense the tension force on the tension member 102. Thus, the first sensor 206 could measure tension forces before, during, and/or after load testing. Further, the first sensor 206 could be used to calibrate the system before, during, and/or after load testing. The first sensor 206 may transmit force information to the control system 120 on a continuous basis, a periodic basis, or in response to a prompt from the control system 120. In some embodiments, tension information from the first sensor 206 could be used to "pre-load" the tension member 102 with a base tension force prior to beginning transverse mode testing. As discussed below, the control system 120 may be configured to control the first actuator 108 based, at least in part, on data received from the first sensor 206. Additionally or alternatively, the control system 120 may be configured to control the second actuator 110 based, at least in part, on data received from the first sensor 206.

In some embodiments, the second sensor 210 could be configured to measure the displacement, angle, or rotation of the second loading member 106 with respect to a reference angle or reference point. The reference angle could relate to an angle based on the current position of the tension member 102, the second loading member 106 or the coupler 208. Other reference angles are possible. The reference point could be a point along an axis oriented in the first direction 112 or any other point associated with the position of the tension member 102, coupler 208, the second loading member 106, or the second actuator 110. Other reference points are possible. The second sensor 210 could be located on or near the secondary loading member 106, the coupler 208, the second actuator 110, or the frame 116. Other locations for the second sensor 210 are possible. The second sensor 210 could include an optical encoder or a magnetic encoder operable to sense position and/or orientation of system components. For example, a magnetic linear encoder could be mounted near a shaft of the second actuator 110. The magnetic linear encoder could be configured to sense a position with respect to a magnetic reference attached to the shaft of the second actuator 110. In some implementations, the second sensor 210 may be a rotary encoder that senses angular position information of the second loading member 106 before, during, and/or after displacement of the second loading member 106. Other configurations for the second sensor 210 are possible. For example, the second sensor 210 could be configured to measure the displacement or angle of the tension member 102 or the coupler 208. Alternatively, the second sensor 210 could be an optical image sensor or a camera. In some embodiments, the second sensor 210 could be configured to transmit angular and/or positional information on a continuous basis to the control system 120. In other embodiments, the second sensor 210 could be configured to transmit angular and/or positional information to the control system 120 on a periodic basis, or to transmit such data in response to a signal from the control system 120. As discussed below, the control system 120 could be configured to control the second actuator 110 based, at least in part, on the data received from the second sensor 210.

Some implementations could include a third sensor (not shown), such as a pressure transducer. In such implementations, the third sensor may be configured to sense a pressure of a hydraulic or pneumatic cylinder. The third sensor could be located, for instance, on a tee at the cylinder end port of the first actuator 108. The third sensor could be configured to sense pressure data for use by the control system 120. Such pressure data could be used by the control system 120, for example, to determine the tensile load on the tension member 102.

The control system 120 could utilize information from the first sensor 206, the second sensor 210, and/or the third sensor to establish a cycle load profile. The cycle load profile could include information about the tensile load on the tension member 102 throughout one or more loading cycles (base load, peak load, cycle period, etc.).

Figure 2B:
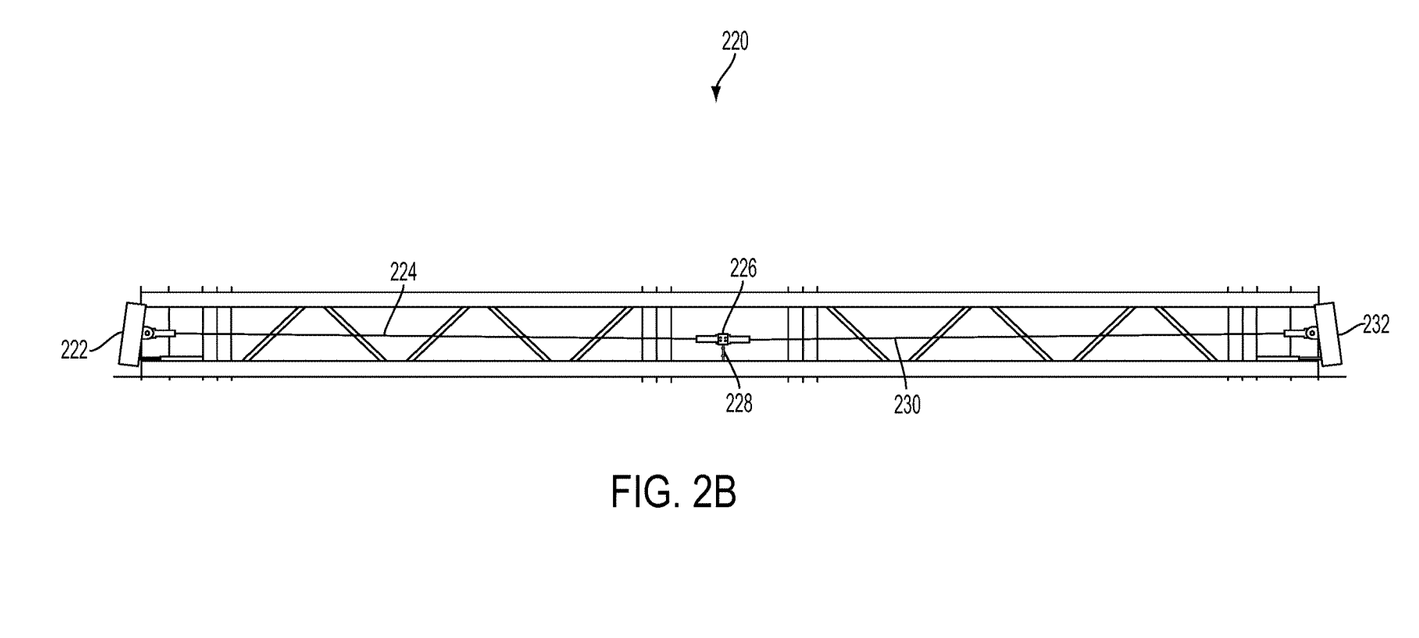
FIG. 2B is a diagram illustrating details of the transverse resonance fatigue test system with multiple tension members, according to an illustrative embodiment.

FIG. 2B is a simplified diagram illustrating selected details of a multiple tension member testing system 220. In some embodiments, such a system could be configured to test two or more tension members simultaneously or at different times. For example, a first tension member 224 could be connected to a first loading member 222 and a coupler 226. The coupler 226 could be connected to an actuator 228. A second tension member 230 could also be connected to the coupler 226. The other end of the second tension member 230 could be connected to a second loading member 232. The first loading member 222 and the second loading member 232 could be configured to move in a direction substantially along the long axis of the tension members. Alternatively, the second loading member 232 need not be configured to move. That is, the second loading member 232 could be a fixed connection point for the second tension member 230. The actuator 228 could be configured to move in two or more directions substantially transverse to the long axis of the tension members. In other words, a single actuator could be configured to move back and forth in a direction transverse to one or more axial directions so as to test multiple tension members simultaneously. Although two tension members are shown in FIG. 2B, more than two tension members could be tested in such an embodiment. For example, multiple tension members could be loaded in parallel between the first loading member 222 and the second loading member 232. Yet further, in reference to FIG. 1, the second loading member 106 could be replaced with a second tension member. Other arrangements of tension members and loading members are possible.

Figure 2C:
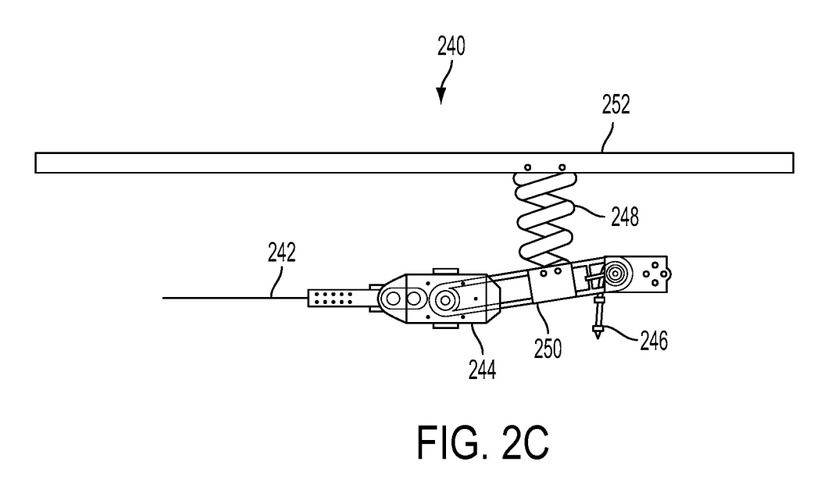
FIG. 2C is a diagram illustrating details of the transverse resonance fatigue test system with a flexible element, according to an illustrative embodiment.

FIG. 2C is a simplified diagram illustrating selected details of a tension member testing system 240 with a flexible element. In an effort to modify, adjust, or optimize the resonant frequency of the loading system, embodiments may further include one or more flexible elements, such as a spring. For instance, as shown in FIG. 2C, the system may further include a flexible element 248 located between the frame 252 and the second loading member 250, located between the frame 252 and the coupler 244, and/or located between the frame 252 and the second actuator 246. And, as shown in FIG. 2C, the flexible element 248 may be located between the coupler 244 and the second actuator 246.

In such implementations, the flexible element 248 may compensate for a gravitational force on the coupler 244 and/or the second loading member 250 during the oscillation of the tension member testing system 240. In various embodiments, the flexible element 248 could include an in-line spring (e.g., connected between the second loading member 250 and the tension member 242), transverse springs (e.g., connected between the tension member 242 and the frame 252), and, in some embodiments, tuned mass dampers. Accordingly, in an illustrative embodiment, a spring could be connected between the coupler and the load frame in order to counteract gravity's effect of differences in peak load at the lower and upper extremes of tension member movement. Although one flexible element 248 is shown in FIG. 2C, multiple flexible elements are possible and the position of the one or more flexible elements could vary. For example, the flexible element 248 could be connected to or incorporated into the coupler 244. Other positions for the flexible element 248 are possible.

Figure 3:
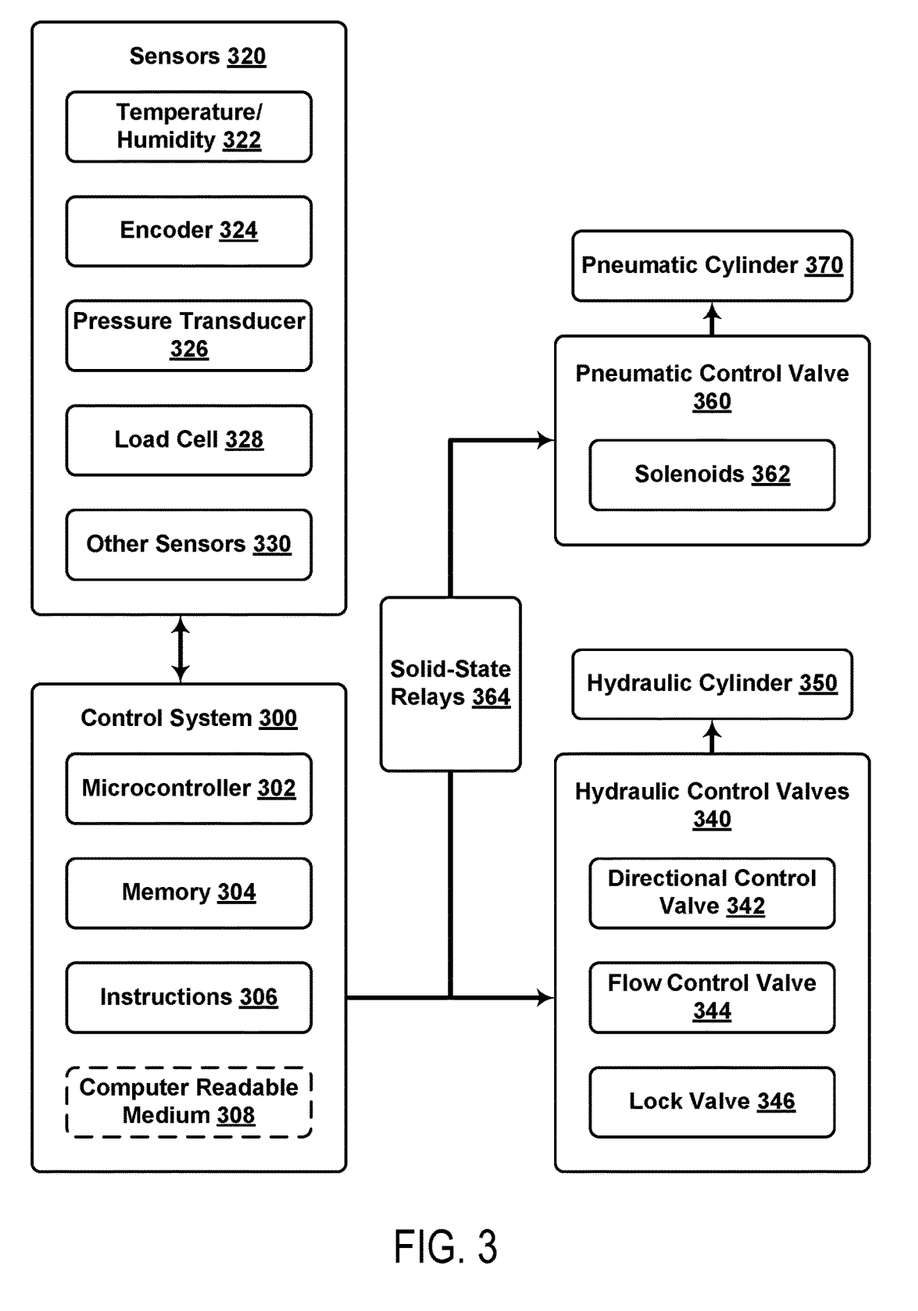
FIG. 3 is a simplified block diagram illustrating various components of the transverse resonance fatigue test system, according to an illustrative embodiment.

FIG. 3 is a simplified block diagram of selected elements of a tension member testing system. A control system 300 could include a microcontroller 302, memory 304, instructions 306, and a computer-readable medium 308. The system could include one or more sensors 320, including a temperature/humidity sensor 322, an encoder 324, a pressure transducer 326, and a load cell 328. Other sensors 330 are also possible. The system could further include solid state relays 364, a pneumatic cylinder 370 and an associated pneumatic control valve 360 and solenoids 362. Additionally, the system could include a hydraulic cylinder 350 and associated hydraulic control valves 340, which could include, for example, a directional control valve 342, a flow control valve 344, and a lock valve 346.

The first actuator 108 and the second actuator 110 could take different forms in various embodiments. For instance, as shown in FIG. 3, the first actuator 108 may be a hydraulic cylinder 350 configured to apply hydraulic forces to the first loading member 104 such that a tensile force is applied to the tension member 102 in the first direction 112. In such implementations, the hydraulic cylinder 350 may include a power unit (such as a pump, not shown). In other examples, the first actuator could be a load screw, a jack, and/or one or more counterweights.

Moreover, in some implementations, the second actuator 110 may be a pneumatic cylinder 370 that is configured to push and/or pull the second loading member 106 via pneumatic forces, such that the second loading member 106 is displaced along two or more directions 114 that are substantially transverse to the first direction 112. Specifically, the pneumatic cylinder 370 could be a single- or double-acting pneumatic cylinder that may utilize a compressed gas, such as air, to produce a linear force. Moreover, in such implementations, the pneumatic cylinder 370 may by controlled by the pneumatic control valve 360. For example, the pneumatic control valve 360 could be a three-position, four-way valve that could be configured to be controlled by the control system 300. The pneumatic control valve 360 could include solenoids 362 that could be configured to adjust the state of the pneumatic control valve 360. For example, the pneumatic control valve 360 could be configured to extend and/or retract a rod of pneumatic cylinder 370. Additionally, the pneumatic valve 360 could be configured to operate in a vented state, where the pneumatic cylinder 370 may be substantially free-moving/floating. In other examples, the second actuator 110 could be a voice coil/solenoid, a direct drive electric motor, and/or one or more masses offset on a rotary motor (or located in-line with suitable hydraulics or pneumatics).

Further shown in FIG. 3, the control system 300 could include one or more computers and/or one or more microcontrollers, such as an Arduino Mega 2560 R3 hardware board. In some examples, the microcontroller 302 could be an 8-bit Atmel flash microcontroller or a 32-bit ARM instruction-based processor. Other types of computers and/or microcontrollers are possible. The microcontroller 302 could include a USB port and/or a RS-232 serial port. The microcontroller 302 could also include analog and/or digital input/output pins. The memory 304 could represent internal memory, such as on-board flash memory. Alternatively or additionally, the memory 304 could represent external memory, such as an SD card. The microcontroller 302 could additionally include a shield that could be configured to provide, for instance, WiFi/internet connectivity. The shield could also be configured to provide an external memory interface, such as a micro SD slot. The control system 300 could be configured to perform various operations based on instructions 306 that could reside, for instance, in memory 304. In some embodiments, a computer-readable medium 308 could include various combinations of memory 304, instructions 306, and the microcontroller 302. The control system 300 could include one or more solid state relays 364. The solid state relays 364 could be configured, in response to a signal from the microcontroller 302, to provide 120 VAC to the pneumatic control valve 360. The pneumatic control valve 360 could be configured to control various aspects of the second actuator 110. For example, in the embodiments where the second actuator 110 is a pneumatic cylinder 370, a solenoid 362 could change or maintain a given valve position of the pneumatic control valve 360 in response to the 120 VAC provided by the solid state relays 364. In such a manner, the control system 300 could be configured to control the pneumatic control valve 360 and the force applied to a rod of the pneumatic cylinder 370. Accordingly, the control system 300 could be configured to control the direction of the force applied to the second loading member 106 (pushing, pulling, or none/freely-float). Accordingly, the control system 300 may be configured to indirectly affect the peak sinusoidal force in the tension member 102.

The control system 300 could also be configured to control the first actuator 108. For example, the control system 300 could be configured such that an analog or digital input to the control system 300 includes output from a pressure transducer 326 and/or the load cell 328. In such an example, the microcontroller 302 could be configured to adjust the position of a rod of the first actuator 108 (which could be a hydraulic cylinder) by controlling the hydraulic control valves 340 (e.g., directional control valve 342, lock valve 346, flow control valve 344) in response to a signal from the pressure transducer 326 and/or the load cell 328. Specifically, the control system 300 may be configured to control the first actuator 108, such that the first loading member 104 applies an initial base load on tension member 102. Alternatively or additionally, the control system 300 could be configured to control the first actuator 108 such that the first loading member 104 applies a tension force on tension member 102 based on, for instance, a desired tension force range. In other examples, the force applied by the first actuator 108 to the first loading member 104 may vary based on changes in one or more parameters of the frame 116 (e.g., expansion and/or contraction of the frame 116 based on temperature loading).

The control system 300 could be additionally configured to control the second actuator 110. As described above, the second actuator 110 could be a pneumatic cylinder 370. In such an embodiment, in response to an input from the second sensor 210, the control system could control a solid state relay 364 to supply 120 VAC to one or more solenoids 362 associated with the pneumatic control valve 360. The 120 VAC signal could cause the one or more solenoids 362 to change the current configuration of pneumatic control valve 360. The behavior of the pneumatic cylinder 370 may be based on the current configuration of pneumatic control valve 360. Accordingly, the control system 300 could be configured to control the pneumatic cylinder 370 to extend and/or retract a rod (or "freely-float"). Specifically, the control system 300 could be configured to control the second actuator 110 such that the loading system enters a transverse mode resonance state at or near a resonance frequency of the loading system. The control system 300 could be further configured to control the second actuator 110 so as to control the amplitude of vibration of the loading system such that the tension force in tension member 102 follows a desired cyclic loading profile. The desired cyclic loading profile could be based on a base load and a peak load. The base load could be an initial base tension applied to the tension member 102. The peak load could be the tension force in the tension member 102 at a maximum displacement of the coupler 208 during the vibration of the loading system. The control system 300 could be configured to perform other functions.

The control system 300 could be configured to accept signals from environmental sensors, such as humidity, altitude, and/or temperature sensors. Correspondingly, the control system 300 could be configured to adjust various control parameters based on, for example, environmental conditions.

The control system 300 could be configured to continuously or periodically monitor and adjust the first actuator 108 and/or the second actuator 110 so as to maintain the tension member 102 in a transverse mode at or near a resonant frequency. For example, the control system 300 could be further configured to determine the current tensile load on the tension member 102 and maintain the tensile load within a desired tensile load range. Additionally or alternatively, the control system 300 could maintain the tensile load on tension member 102 based on the cycle load profile.

The first loading member 104 and the second loading member 106 could take various different forms in various different embodiments. In some implementations, the first loading member 104 and the second loading member 106 may be one or more steel structures, such as beams. As shown in FIGS. 1 and 2, the second loading member 106 may have a dimension that is less than a respective dimension of the tension member 102. For instance, the second loading member 106 may have a length of 3 feet, and the tension member 102 may have a length of 30 feet. In some examples, the second loading member 106 may include one or more bearings (e.g., cylindrical or linear roller bearings, not shown) that may reduce energy losses during the oscillation of the second loading member 106, such as energy losses due to friction.

In other examples, the second loading member 106 may be a combination of one or more structures and cables, such as a four-bar (or cable) linkage. In such examples, the second loading member 106 may include one or more cables configured to stabilize or reduce out-of-plane motion of the second loading member 106 during the oscillation of the second loading member 106.

In other examples, the second loading member 106 may be similar or identical to any of the tension members described herein. In such examples, one or more parameters of the tension member 102 and the second loading member 106 may be tested simultaneously.

As noted above, embodiments described herein may be used to test stiffness and/or strength of tension members (e.g., monotonic tensile tests). For instance, in some examples, the second loading member 106 may be removed, and the tension member 102 may be directly connected to the frame 116. Further, in such examples, the first sensor 206 and/or the third sensor may sense information during the test. Other equipment may be used as well, including an extensomers, visual markers, and one or more cameras.

The tension member 102 could include, for example, a high-tensile-strength core constructed of carbon fiber, steel, or other suitable material. The core could be surrounded by strands of an electrically-conductive material, such as aluminum alloy. The tension member 102 could also include instrumentation for measuring position, angle, and/or forces, such as tension. Such instrumentation could be incorporated into the tension member 102 itself, or could be mounted on the tension member 102.

Note that, although the tension member 102 may be described as a tether used as part of an AWT, the embodiments described herein may also be used to test tension members for use in other applications, and/or to test other types of tension members including ropes, cables, umbilicals, etc. used in variety of applications, such as overhead transmission, aerostats, offshore drilling, ROVs, towing, mining, and/or bridges, among other possibilities.

III. Illustrative Methods

Figure 4:
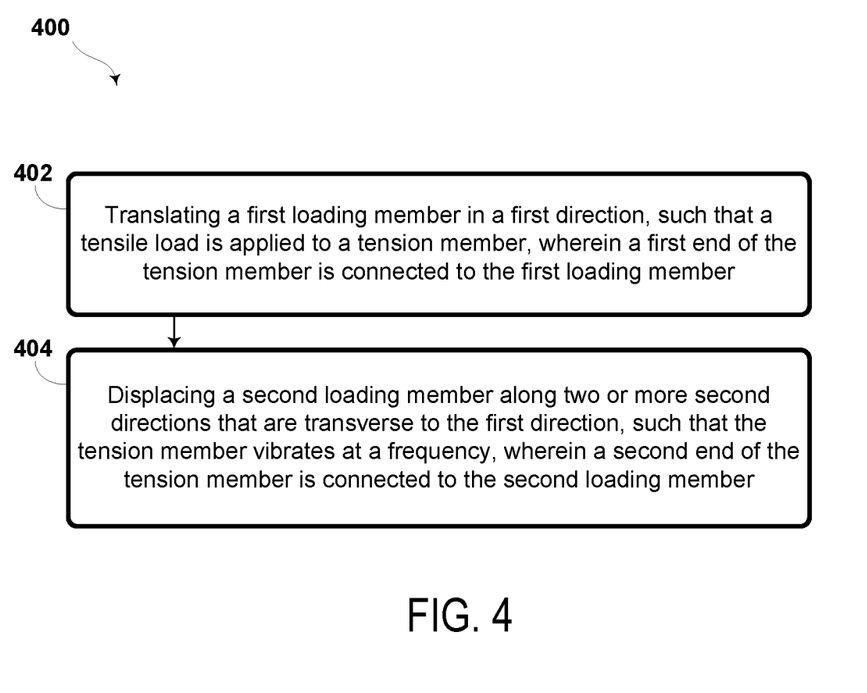
FIG. 4 is a simplified block diagram illustrating a method, according to an illustrative embodiment.

A method 400 is provided for applying tension forces to a tension member by, for example, causing the tension member to oscillate in a transverse mode. The method could be performed using any of the apparatus shown in FIGS. 1-3 and described above. However, other configurations could be used. FIG. 4 illustrates the blocks of an example method with reference to FIGS. 1-3. However, it should be understood that in other embodiments, the blocks may appear in different order and blocks could be added or subtracted.

Block 402 includes translating the first loading member 104 in the first direction 112. In doing so, a tensile load could be applied to the tension member 102. In such a case, the first end of the tension member 102 could be connected to the first loading member 104. The translating of the first loading member 104 could be performed in various ways. For example, the control system 300 could control the first actuator 108 to apply a force to the first loading member 104 so as to apply a tension force to tension member 102. In some embodiments, the load applied to tension member 102 could be measured by the load cell 328. Additionally or alternatively, the load could be measured indirectly by the pressure transducer 326. The control system 300 could control the first actuator 108, for example, by adjusting the hydraulic control valves 340 associated with the first actuator 108 in response to information from the load cell 328 and/or the pressure transducer 326. In other embodiments, the first loading member 104 could be translated in the first direction 112 using other mechanical features and/or components such as a load screw, a jack, and/or one or more counterweights.

Block 404 includes displacing the second loading member 106 along two or more second directions 114 that are transverse to the first direction 112 such that the tension member 102 vibrates at a frequency wherein the second end of the tension member 102 is connected to the second loading member 106. In some examples, the second actuator 110 may apply one or more forces to the second loading member 106 at one or more forcing frequencies to cause the second loading member 106 to vibrate. In such implementations, the one or more forcing frequencies may vary during the one or more oscillation cycles. The frequency at which the second loading member 106 vibrates could include, for example, a resonant frequency of a combination of loading system elements that could include the tension member 102, the coupler 208, and/or other loading system elements.

It may be beneficial for the forces applied to the second loading member 106 to be substantially in phase with the vibration of the tension member 102. In some examples, a resonant frequency of the combination of loading system elements may vary during the oscillation of the second loading member 106 based, at least in part, on a change in a stiffness of the loading system in the transverse direction. Such a change in stiffness may be due to an amount of deflection of the tension member 102. Accordingly, the control system 300 may control the second actuator 110 to (i) cause the tension member 102 to vibrate at a resonant frequency and (ii) maintain the vibration by controlling an amplitude of the vibration.

In some examples, the resonant frequency of the combination of loading system elements may not be known before cyclic displacement of the second loading member 106. As a result, one or more forcing frequencies may be selected to excite the vibration of the tension member 102. For instance, in some implementations, the one or more forcing frequencies may be selected based on a frequency sweep mode of the control system 300. In the frequency sweep mode, the control system 300 may (i) select a first frequency of the one or more forcing frequencies that is known or believed to be less than the resonant frequency of the combination of loading system elements; and (ii) increase the first frequency of the one or more forcing frequencies until the tension member 102 vibrates at a resonant frequency of the combination of loading system elements. Such an approach may involve the second actuator 110 applying one or more forces to the second loading member 106 that is less than respective forces applied in other modes, such as a step response mode, that could be used to cause vibration of the tension member 102 at a resonant frequency of the combination of loading system elements.

After the tension member 102 is vibrating at the resonant frequency, the control system 300 may control the amplitude of vibration of the tension member 102 by changing a direction of a force applied by the second actuator 110 to the second loading member 106. Further, in such implementations, the control system 300 may change the direction of the force applied to the second loading member 106 at one or more peak displacement locations of the tension member 102. For instance, when the second loading member 106 is configured to move back and forth substantially perpendicular to the ground, the control system 300 may (i) cause the second actuator 110 to apply an upward force to the second loading member 106 until the second loading member 106 translates to a maximum point in the oscillation; (ii) cause the second actuator 110 to apply a downward force to the second loading member 106 until the second loading member 106 translates to a minimum point in the oscillation; and then repeat step (i). Additionally, the control system 300 may cause the second actuator 110 to change the magnitude of one or more forces applied to the second loading member 106 during the displacement of the second loading member 106.

In other implementations, the control system 300 may control the amplitude of vibration of the tension member 102 by causing the second actuator 110 to apply a force to the second loading member 106 during a portion of a single oscillation cycle (which may be referred to as intra-cycle duty cycle). For instance, the control system 300 may cause the second actuator 110 to apply a force to the second loading member 106 during one quarter of an oscillation cycle and allow the second actuator 110 to "freely float" during the rest of the oscillation cycle. Other intra-cycle duty cycle control implementations are possible.

In other implementations, the control system 300 may control the amplitude of vibration of the tension member 102 by causing the second actuator 110 to apply a force to the second loading member 106 during some, but not every oscillation cycle (which may be referred to as inter-cycle duty cycle). For instance, when a vibration of the second loading member 106 includes four oscillation cycles, the control system 300 may cause the second actuator 110 to apply a force to the second loading member 106 during three oscillation cycles of the vibration, but not during the fourth oscillation cycle. Other implementations of the inter-cycle duty cycle control method are possible so as to maintain the tension member 102 vibrating in a transverse mode at a resonant frequency of a combination of loading system elements.

In an illustrative configuration, the control system 300 may control the amplitude of vibration of the tension member 102 by any combination of the techniques described above, including causing the second actuator 110 to change a magnitude of the force, apply the force during a portion of an oscillation cycle, and/or apply the force during multiple oscillation cycles of the vibration.

Furthermore, an illustrative method could include determining a tension load on the tension member 102, determining a velocity of the second actuator 110, and controlling the second actuator 110 such that the tension load is maintained based on a desired base tension load and a desired peak tension load. The desired base tension load could be, for example, the initial base tension applied by displacement of the first loading member 104. The desired peak tension load could be, for example, a desired, known, or anticipated maximum load on tension member 102. Other desired base tension and desired peak tension values are possible.

IV. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A system comprising:
    a tension member having a first end and a second end, wherein the first end of the tension member is connected to a first loading member and the second end of the tension member is connected to a second loading member;
    a load cell;
    a first actuator;
    a second actuator; and
    a control system comprising a processor and a memory, wherein the processor is configured to execute instructions stored in the memory so as to carry out operations, wherein the operations comprise:
        controlling the first actuator to displace the first loading member based on information received from the load cell such that a tensile load is applied to the tension member along a first direction; and
        controlling the second actuator to displace the second loading member based on a desired cyclic loading profile such that the second loading member oscillates between two or more second directions, wherein the oscillation of the second loading member causes the tension member to vibrate at a frequency, and wherein the desired cyclic loading profile comprises a base load and a peak load.

2. The system of claim 1, wherein controlling the first actuator is further based on a desired base tensile load.

3. The system of claim 1, wherein the desired cyclic loading profile further comprises a desired oscillation frequency, and wherein controlling the second actuator is further based on the desired oscillation frequency.

4. The system of claim 1, wherein the operations further comprise controlling the second actuator to control an amplitude of a vibration of the tension member.

5. The system of claim 1, wherein controlling the second actuator causes the tension member to be periodically loaded substantially in tension according to the desired cyclic loading profile.

6. The system of claim 1, wherein the first actuator comprises a hydraulic cylinder, and wherein the second actuator comprises a pneumatic cylinder.

7. The system of claim 1, further comprising a frame;
wherein a first end of the first loading member is connected to the tension member and a second end of the first loading member is connected to the frame;
wherein a first end of the second loading member is connected to the tension member and a second end of the second loading member is connected to the frame;
wherein the frame is configured to resist one or more compressive stresses based on an arrangement of the first loading member, the second loading member, and the tension member.

8. The system of claim 1, further comprising at least one sensor, wherein the operations further comprise receiving information indicative of a position of the second loading member, and wherein controlling the second actuator is further based on the position of the second loading member.

9. The system of claim 1, further comprising at least one sensor, wherein the operations further comprise receiving information indicative of a velocity of the second loading member, and wherein controlling the second actuator is further based on the velocity of the second loading member.

10. The system of claim 1, wherein controlling the second actuator comprises:
while driving a position of the second actuator according to a forcing frequency, adjusting the forcing frequency within a frequency range;
determining a resonant frequency of the tension member based on at least one of: the frequency of vibration of the tension member or an amplitude of the tension member; and
driving the position of the second actuator according to the resonant frequency.

11. A method comprising:
controlling a first actuator to displace a first loading member based on information received from a load cell such that a tensile load is applied to a tension member along a first direction, wherein the tension member has a first end and a second end, wherein the first end of the tension member is connected to the first loading member and the second end of the tension member is connected to a second loading member; and
controlling a second actuator to displace the second loading member based on a desired cyclic loading profile such that the second loading member oscillates between two or more second directions, wherein the oscillation of the second loading member causes the tension member to vibrate at a frequency, and wherein the desired cyclic loading profile comprises a base load and a peak load.

12. The method of claim 11, wherein controlling the first actuator is further based on a desired base tensile load.

13. The method of claim 11, wherein the desired cyclic loading profile further comprises a desired oscillation frequency, and wherein controlling the second actuator is further based on the desired oscillation frequency.

14. The method of claim 11, further comprising controlling the second actuator to control an amplitude of a vibration of the tension member.

15. The method of claim 11, wherein controlling the second actuator causes the tension member to be periodically loaded substantially in tension according to the desired cyclic loading profile.

16. The method of claim 11, wherein the first actuator comprises a hydraulic cylinder, and wherein the second actuator comprises a pneumatic cylinder.

17. The method of claim 11, further comprising receiving, via at least one sensor, information indicative of a position of the second loading member, and wherein controlling the second actuator is further based on the position of the second loading member.

18. The method of claim 11, further comprising receiving, via at least one sensor, information indicative of a velocity of the second loading member, and wherein controlling the second actuator is further based on the velocity of the second loading member.

19. The method of claim 11, wherein controlling the second actuator comprises maintaining the base load and the peak load according to the desired cyclic loading profile.

20. The method of claim 11, wherein controlling the second actuator comprises:
while driving a position of the second actuator according to a forcing frequency, adjusting the forcing frequency within a frequency range;
determining a resonant frequency of the tension member based on at least one of: the frequency of vibration of the tension member or an amplitude of the tension member; and
driving the position of the second actuator according to the resonant frequency.

* * * * *